US006093686A

United States Patent [19]

Nakada et al.

[11] Patent Number: 6,093,686

[45] Date of Patent: Jul. 25, 2000

[54] LIQUID FOR CONTACT LENSES

[75] Inventors: Kazuhiko Nakada; Yutaka Matano, both of Kasugai, Japan

[73] Assignee: Menicon Co., Ltd., Aichi-ken, Japan

[21] Appl. No.: 09/265,544

[22] Filed: Mar. 9, 1999

[30] Foreign Application Priority Data

Mar. 12, 1998 [JP] Japan .................................. 10-061807

[51] Int. Cl.[7] ................................ C11D 3/37; C11D 9/50; A61K 31/13

[52] U.S. Cl. .......................... 510/112; 510/475; 514/839; 514/840; 424/78.04; 422/28

[58] Field of Search ............................ 510/112–115, 475; 514/839–840; 424/78.04; 422/28; 564/463, 509

[56] References Cited

U.S. PATENT DOCUMENTS

| | | | |
|---|---|---|---|
| 4,908,404 | 3/1990 | Benedict et al. | 525/54.11 |
| 5,171,318 | 12/1992 | Gibson et al. | 623/5 |
| 5,461,433 | 10/1995 | Nakabayashi et al. | 351/177 |
| 5,529,986 | 6/1996 | Larsson et al. | 514/54 |
| 5,711,915 | 1/1998 | Siegmund et al. | 422/68.1 |
| 5,782,992 | 7/1998 | Frangione | 134/42 |
| 5,811,151 | 9/1998 | Hendriks et al. | 427/2.24 |

FOREIGN PATENT DOCUMENTS 10319358 12/1998 Japan .

*Primary Examiner*—Kery Fries
*Assistant Examiner*—Dawn L. Garrett
*Attorney, Agent, or Firm*—Browdy and Neimark

[57] ABSTRACT

A liquid for contact lenses, containing a polymer (A) having a recurring unit represented by the formula (I):

(I)

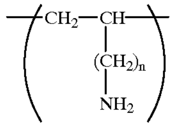

wherein n is 0 or 1. The liquid for contact lenses can considerably decrease variation of the base curve of a contact lens during preservation, and shows excellent antiseptic effect and excellent antibacterial effect.

11 Claims, No Drawings

LIQUID FOR CONTACT LENSES

BACKGROUND OF THE INVENTION

The present invention relates to a liquid for contact lenses. More particularly, the present invention relates to a liquid for contact lenses which can be preferably used for preservation, cleaning and disinfection of contact lenses.

In general, most of contact lenses, in particular oxygen permeable hard contact lenses, are prepared by using a silicone component. Accordingly, the lens surface becomes hydrophobic and wettability of the lens at initial wearing is poor. As a result, wearing sensation is lowered and sight cannot be sufficiently recovered.

Therefore, in order to maintain surface wettability during preservation when not being worn, the above oxygen permeable hard contact lens is subjected to surface treatment or immersed in a preserving solution such as physiological sodium chloride solution.

However, in the case that a contact lens is preserved in such physiological sodium chloride solution, the base curve which is one of the important standards of a contact lens sometimes varies.

For instance, bacteria may propagate in a preserving solution during preservation of a contact lens. Accordingly, in order to prevent bacteria from propagating, an antiseptic is added to the preserving solution.

However, the antiseptic effect of the antiseptic is sometimes insufficient, or some of the antiseptics are poor in safety and durability. Accordingly, such antiseptics are not effective for preventing the propagation of bacteria.

In particular, in the case when a soft contact lens is immersed in the above preserving solution containing an antiseptic, the antiseptic sometimes adheres to the surface of the soft contact lens or is sometimes captured in the inside of the lens. Accordingly, it is desired that there is developed a method comprising using a polymerized antiseptic.

An object of the present invention is to provide a liquid for contact lenses, which can substantially decrease the variation of the base curve of a contact lens, in particular an oxygen permeable hard contact lens during preservation, and which shows an excellent antiseptic effect, an excellent antibacterial effect and durability of these effects.

This and other objects of the present invention will become apparent from the description hereinafter.

SUMMARY OF THE INVENTION

In accordance with the present invention, there is provided a liquid for contact lenses, containing a polymer (A) having a recurring unit represented by the formula (I):

(I)

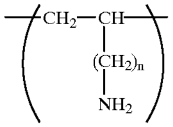

wherein n is 0 or 1.

The liquid for contact lenses of the present invention is excellent in solubility and appearance, has a not unpleasant smell, and shows stability of antiseptic effect and antibacterial effect for a long period of time. Therefore, when a contact lens, in particular, an oxygen permeable hard contact lens is preserved in the liquid for contact lenses of the present invention, variation of the base curve which is one of important standards of a contact lens can be considerably decreased.

DETAILED DESCRIPTION

The liquid for contact lenses of the present invention contains a polymer (A) having a recurring unit represented by the formula (I):

(I)

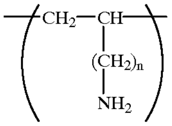

wherein n is 0 or 1.

In the liquid for contact lenses, the above polymer (A) is an effective ingredient for decreasing the variation of base curve of a contact lens during preservation and further imparting an antiseptic effect and an antibacterial effect.

In the present invention, because the variation of the base curve of a contact lens can be considerably decreased and the antiseptic effect and antibacterial the effect can be greatly exhibited, a polyallylamine having a recurring unit represented by the formula:

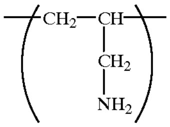

is preferably used.

In order to sufficiently provide stability of the base curve of a contact lens and sufficiently provide an antiseptic effect and antibacterial an effect, the polymer (A) needs to have a certain molecular weight. Accordingly, it is desired that weight average molecular weight of the polymer (A) is at least about 500, preferably at least about 1000. In order to remove fears that solubility of the polymer (A) in a medium such as water is reduced so that a uniform liquid for contact lenses cannot be easily prepared, and that handling of the polymer (A) is reduced due to increase of viscosity, it is desired that weight average molecular weight of the polymer (A) is at most about 200000, preferably at most about 100000.

Various polymers (A) can be used alone or in admixture thereof.

In order to sufficiently decrease variation of base curve of a contact lens during preservation and further sufficiently provide both an antiseptic effect and an antibacterial effect, it is desired that the content of the polymer (A) in the liquid for contact lenses is at least 0.01 w/v %, preferably at least 0.1 w/v %. In order to remove a fear that a contact lens is easily stained when dried and handling is lowered because viscosity of the liquid for contact lenses is too great, it is desired that the content of the polymer (A) in the liquid for contact lenses is at most 10 w/v %, preferably at most 3 w/v %.

The liquid for contact lenses can contain, for instance, an antiseptic, a chelating agent and the like in addition to the above polymer (A).

The above antiseptic is a component for preventing contamination for the liquid for contact lenses with germs and preventing contamination for a contact lens with bacteria during preservation in the liquid for contact lenses. By using the added antiseptic, the antiseptic effect and antibacterial effect which are exhibited from the polymer (A) can be further increased.

The antiseptic is an ophthalmic physiologically acceptable component and is not particularly limited. Typical examples of the added antiseptic are, for instance, a mercury antiseptic such as mercury phenyl nitrate, mercury phenyl acetate or thimerosal; a surface active agent type antiseptic such as benzalkonium chloride or pyridinium bromide; an alcohol antiseptic such as chlorhexidine, polyhexamethylene biguanide or chlorobutanol; methylparaben, propylparaben, dimethyloldimethylhydantoin, imidazoliumurea; and the like. These can be used alone or in admixture thereof.

In order to sufficiently exhibit further antiseptic effect, it is desired that the content of the added antiseptic in the liquid for contact lenses is at least 0.00001 w/v %, preferably at least 0.00003 w/v %. When the content of the added antiseptic in the liquid for contact lenses is too large, there are adverse tendencies that the antiseptic directly inserts into that eyes, so that eyes are injured, and that some of the antiseptics impart adverse influence to standards and properties of a contact lens. Accordingly, it is desired that the content of the added antiseptic in the liquid for contact lenses is at most 0.5 w/v %, preferably at most 0.3 w/v %.

The above noted added chelating agent is a component for preventing calcium, which is included in the liquid for contact lenses or lacrimal fluid adhering a contact lens, from accumulating on a contact lens.

The chelating agent is an ophthalmic physiologically acceptable component and is not particularly limited. Typical examples of the chelating agent are, for instance, ethylenediaminetetraacetic acid, sodium ethylenediaminetetraacetate, phytic acid, citric acid and the like. These can be used alone or in admixture thereof.

In order to sufficiently exhibit effect of preventing accumulation of calcium on a contact lens, it is desired that the content of the chelating agent in the liquid for contact lenses is at least 0.001 mol/l, preferably at least 0.0015 mol/l. When the content of the chelating agent in the liquid for contact lenses is too large, there is a tendency that effects are not very much improved considering the content, so economy is lowered. Accordingly, it is desired that the content of the chelating agent in the liquid for contact lenses is at most 0.1 mol/l, preferably at most 0.05 mol/l.

The liquid for contact lenses can contain, for instance, other additives such as a buffer, an isotonizing agent, a thickener and a surface active agent in addition to the antiseptic and the chelating agent.

The above buffer is a component for setting pH of the liquid for contact lenses within the range of about 5 to 9 near to pH of lacrimal fluid, preventing variation of the pH of the liquid for contact lenses, due to any outside influence, and protecting shape and optical property of a contact lens during preservation.

The buffer is an ophthalmic physiologically acceptable component and is not particularly limited. Typical examples of the buffer are, for instance, boric acid, sodium borate, phosphoric acid, sodium phosphate, citric acid, sodium citrate, lactic acid, sodium lactate, glycine, an amino acid such as glutamic acid, sodium salt of an amino acid, malic acid, sodium malate and the like. These can be used alone or in admixture thereof.

In order to sufficiently exhibit buffer effect, it is desired that the content of the buffer in the liquid for contact lenses is at least 0.005 mol/l, preferably at least 0.01 mol/l. When the content of the buffer in the liquid for contact lenses is too large, there is a tendency that buffer effect is not very much additionally improved and osmotic pressure is heightened, so an adverse influence is imparted to shape of a contact lens. Accordingly, it is desired that the content of the buffer in the liquid for contact lenses is at most 0.5 mol/l, preferably at most 0.15 mol/l.

The above isotonizing agent is a component for setting osmotic pressure of the liquid for contact lenses within the range of 280 to 320 mOs/kg near to osmotic pressure of lacrimal fluid, and supporting maintenance of shape of a contact lens during preservation.

The isotonizing agent is an ophthalmic physiologically acceptable component and is not particularly limited. Typical examples of the isotonizing agent are, for instance, an inorganic salt such as sodium chloride, potassium chloride or calcium chloride; compounds which are exemplified as the above buffer; and the like. These can be used alone or in admixture thereof.

In order to sufficiently impart osmotic pressure to the liquid for contact lenses, it is desired that the content of the isotonizing agent in the liquid for contact lenses is at least 0.01 mol/l, preferably at least 0.05 mol/l. When the content of the isotonizing agent in the liquid for contact lenses is too large, there is a tendency that osmotic pressure is heightened, so an adverse influence is imparted to shape of a contact lens. Accordingly, it is desired that the content of the isotonizing agent in the liquid for contact lenses is at most 0.5 mol/l, preferably at most 0.15 mol/l.

The above noted is a component for protecting a contact lens from outside stress during preservation.

The thickener is an ophthalmic physiologically acceptable component and is not particularly limited. Typical examples of the thickener are, for instance, a viscous substance such as polyvinyl alcohol, poly-N-vinylpyrrolidone, polyacrylamide, hydrolyzate of polyacrylamide, polyacrylic acid, xanthane gum, hydroxyethylcellulose, carboxymethylcellulose, methylhydroxyethylcellulose, methylhydroxypropylcellulose, methylcellulose, sodium alginate, polyethylene glycol, gelatin, sodium chondroitin sulfate or gum arabic; and the like. These can be used alone or in admixture thereof.

In order to sufficiently protect a contact lens from outside stress during preservation, it is desired that the content of the thickener in the liquid for contact lenses is at least 0.01 w/v %, preferably at least 0.02 w/v %. When the content of the thickener in the liquid for contact lenses is too large, there is a tendency that the liquid for contact lenses becomes gelated, so the preservative property is lowered. Accordingly, it is desired that the content of the thickener in the liquid for contact lenses is at most 10 w/v %, preferably at most 5 w/v %.

The above surface active agent is a component for further improving the cleaning effect of the liquid for contact lenses.

The surface active agent is an ophthalmic physiologically acceptable component and is not particularly limited. Various surface active agents such as an anionic surface active agent, a nonionic surface active agent and a combination of anionic surface active agent with nonionic surface active agent can be used.

Typical examples of the anionic surface active agent are, for instance, sodium alkylsulfate sodium alkylbenzenesulfonate, sodium alkyloylmethyltaurinate, sodium alkyloylsarcosinate, sodium α-olefinsulfonate, sodium polyoxyethylene alkyl ether phosphate, sodium polyoxyethylene alkyl ether sulfate, sodium polyoxyethylene alkyl phenyl ether sulfate, sodium di(polyoxyethylene alkyl ether) phosphate and the like. These can be used alone or in admixture thereof. Among them, sodium alkylsulfate, sodium alkylbenzenesulfonate, sodium α-olefinsulfonate, sodium polyoxyethylene alkyl ether sulfate and sodium polyoxyethylene alkyl phenyl ether sulfate show excellent cleaning effect, and are preferable. When these anionic surface active agents are used with the nonionic surface active agent, effective cleaning effect is exhibited during immersion and preservation for a short period of time.

In order to sufficiently exhibit cleaning effect, it is desired that the content of the anionic surface active agent in the liquid for contact lenses is at least 0.01 w/v %, preferably at least 0.02 w/v %. When the content of the anionic surface active agent in the liquid for contact lenses is too large, there is a tendency that cleaning effect is not very much further improved and hands become rough. Accordingly, it is desired that the content of the anionic surface active agent in the liquid for contact lenses is at most 10 w/v %, preferably at most 5 w/v %.

Typical examples of the nonionic surface active agent are, for instance, an adduct of higher alkylamine with polyethylene glycol, an adduct of higher fattyamide with polyethylene glycol, an ester of polyglycerin with higher fatty acid, an ester of a polyalkylene glycol such as polyethylene glycol with higher fatty acid, a polyethylene glycol copolymer ester, an ester of adduct (of polyvalent alcohol with polyethylene glycol) with higher fatty acid, an ether of polyethylene glycol with higher alcohol, an ether of polyglycerin with higher alcohol, an ether of polyethylene glycol with alkylphenol, a condensate of ether (of polyethylene glycol with alkylenephenol) with formaldehyde, a polypropylene glycol-polyethylene glycol copolymer, a phosphate, castor oil, hydrogenated castor oil, a sorbitan alkylester of polyethylene glycol, an adduct of sterol with polyethylene glycol, poloxamer and the like. These can be used alone or in admixture thereof. Among them, an ether of polyethylene glycol with higher alcohol, an ester of polyethylene glycol with higher fatty acid, an ester of polyglycerin with higher fatty acid, an ether of polyethylene glycol with alkylphenol, a sorbitan alkylester of polyethylene glycol and poloxamer show excellent cleaning effect, and are preferable.

In order to sufficiently exhibit cleaning effect, it is desired that the content of the nonionic surface active agent in the liquid for contact lenses is at least 0.01 w/v %, preferably at least 0.02 w/v %. When the content of the nonionic surface active agent in the liquid for contact lenses is too large, there is a tendency that cleaning effect is not very much more improved and hands become rough. Accordingly, it is desired that the content of the nonionic surface active agent in the liquid for contact lenses is at most 10 w/v %, preferably at most 5 w/v %.

When the anionic surface active agent and the nonionic surface active agent are used at the same time, it is desired that the content of the anionic surface active agent and the content of the nonionic surface active agent are within the above defined range, respectively. Also, it is desired that the total amount of the anionic surface active agent and the nonionic surface active agent in the liquid for contact lenses is 0.02 to 20 w/v %, preferably 0.05 to 10 w/v %.

The liquid for contact lenses of the present invention contains the polymer (A) as an effective ingredient and, as occasion demands, contains the antiseptic, the chelating agent and the other additives. As a medium, water such as distilled water or purified water may be contained in the liquid for contact lenses. The amount of an aqueous medium such as water is adjusted so that the total amount of the liquid for contact lenses reaches 100%.

For instance, the polymer (A) is added to the prescribed amount of the aqueous medium and, as occasion demands, the additives such as antiseptic, chelating agent, buffer, isotonizing agent, thickener and surface active agent are added thereto. These are sufficiently mixed and stirred with each other, and the polymer (A) and the additives are dissolved in the aqueous medium to give a solution. Then, the solution is filtrated to give the liquid for contact lenses of the present invention.

Viscosity of the liquid for contact lenses is not particularly limited. In consideration of handling during preservation of a contact lens, it is preferable that viscosity of the liquid for contact lenses is at most about 200 cP at 25° C.

It is preferable that pH of the liquid for contact lenses is 5 to 9, which is much the same as pH of lacrimal fluid.

In the case that various contact lenses are immersed in the thus obtained liquid for contact lenses of the present invention, the various contact lenses can be preserved with hardly varying the base curve thereof. In addition, contamination for the liquid for contact lenses itself with bacteria can be prevented and various contact lenses can be cleaned or disinfected in the liquid for contact lenses.

The liquid for contact lenses of the present invention can be suitably used as a preserving solution, a cleaning solution, a disinfecting solution or a liquid used for at least two of preservation, cleaning and disinfection.

A contact lens can be preserved, cleaned or disinfected by entirely immersing itself in the liquid for contact lenses in the prescribed vessel and sealing up the vessel.

A contact lens which is preserved, cleaned or disinfected in the liquid for contact lenses is not particularly limited. Various contact lenses such as a water-absorptive contact lens and a non-water-absorptive contact lens can be applied. Also, various contact lenses such as a soft contact lens and a hard contact lens can be applied. Even if an oxygen permeable hard contact lens prepared by polymerizing a monomer mixture containing silicone compounds such as a siloxanyl (meth)acrylate monomer, a siloxanylstyrene monomer, a siloxanyl fumarate and a siloxanyl itaconate is immersed in the liquid for contact lenses, variation of base curve of the oxygen permeable hard contact lens can be considerably decreased during preservation.

The liquid for contact lenses of the present invention is more specifically described and explained by means of the following Examples. It is to be understood that the present invention is not limited to the Examples, and various changes and modifications may be made in the invention without departing from the spirit and scope thereof.

EXAMPLE 1

Polyallylamine having a weight average molecular weight of about 10000 and a recurring unit represented by the formula:

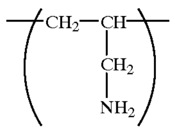

(hereinafter referred to as polyallylamine (1)) was added to distilled water. They were stirred at room temperature or with slightly heating for about 60 minutes to dissolve polyallylamine (1) in the distilled water. The obtained solution was filtrated to give 300 ml of a preserving solution for contact lenses, containing 0.5 w/v % of polyallylamine (1).

Solubility, appearance, unpleasant or bad smell, pH and viscosity of the preserving solution for contact lenses were examined according to the following methods. The results are shown in Table 1.

(i) Solubility

Existence of insoluble components in the preserving solution for contact lenses was examined with naked eyes and evaluated according to the following criteria for evaluation.

Criteria for Evaluation

A: There are no insoluble components at all.

B: There is a slight insoluble component.

C: There are remarkably many insoluble components.

(ii) Appearance

Appearance of the preserving solution for contact lenses was observed with naked eyes and evaluated according to the following criteria for evaluation.

Criteria for Evaluation

A: The preserving solution is uniform and transparent.

B: The preserving solution is slightly cloudy in white.

C: The preserving solution is remarkably cloudy in white.

(iii) Bad Smell

Existence of bad smell of the preserving solution for contact lenses was examined at a distance of 5 cm and evaluated according to the following criteria for evaluation.

Criteria for Evaluation

A: Bad smell is not perceived at all.

B: Bad smell is slightly perceived.

C: Bad smell is remarkably perceived.

(iv) pH

Using glass electrode type pH meter (HORIBA pH METER F-13 made by Horibaseisakusho Co., Ltd.), pH of the preserving solution for contact lenses was measured at 25° C.

(v) Viscosity

Using B type viscosimeter, viscosity (cP) of the preserving solution for contact lenses was measured at 25° C.

Then, a monomer mixture of 50 parts by weight of siloxanyl methacrylate, 40 parts by weight of trifluoroethyl methacrylate, 10 parts by weight of methyl methacrylate and 5 parts by weight of ethylene glycol dimethacrylate was copolymerized to give a polymer. The polymer was molded to give an oxygen permeable hard contact lens having a thickness of 0.12 mm.

Each base curve of five pieces of the above oxygen permeable hard contact lens was previously measured. Then, the average base curve of the above five contact lenses before maintenance was calculated.

The five oxygen permeable hard contact lenses and the preserving solution for contact lenses were put in a case for contact lenses. The five oxygen permeable hard contact lenses were immersed in the preserving solution for contact lenses, and the case was sealed up and maintained at 40° C. After 2 weeks and 4 weeks, each base curve of the five oxygen permeable hard contact lenses was measured.

According to the difference between base curve of the contact lens after maintenance and previously measured base curve of the contact lens, the variation of each base curve was calculated. Then, the average variation of base curve of the five contact lenses was calculated. Using the average base curve of the five contact lenses before maintenance and the average variation of base curve of the five contact lenses, the variation coefficient of base curve (%) was calculated according to the following equation. The results are shown in Table 1.

Variation coefficient of base curve (%)={(Average variation of base curve)/(Average base curve before maintenance)}×100

COMPARATIVE EXAMPLE 1

The variation coefficient of base curve was calculated in the same manner as in Example 1 except that physiological sodium chloride solution was used instead of the preserving solution for contact lenses in Example 1. The results are shown in Table 1.

EXAMPLE2

In the same manner as in Example 1 except that 0.5 ppm (weight) of polyhexamethylene biguanide and 1 w/v % (0.033 mol/l) of ethylenediaminetetraacetic acid were added to distilled water together with 0.5 w/v % of polyallylamine (1) in Example 1, 300 ml of a cleaning and disinfecting solution for contact lenses was prepared.

Solubility, appearance, unpleasant smell, pH and viscosity of the cleaning and disinfecting solution for contact lenses were examined in the same manner as in Example 1. The results are shown in Table 1.

Using the cleaning and disinfecting solution for contact lenses instead of the preserving solution for contact lenses in Example 1, the variation coefficient of base curve was calculated in the same manner as in Example 1. The results are shown in Table 1.

EXAMPLE 3

In the same manner as in Example 1 except that 0.1 w/v % of poloxamer and 0.1 w/v % (0.0033 mol/l) of ethylenediaminetetraacetic acid were added to distilled water together with 0.5 w/v % of polyallylamine (1) in Example 1, and further isotonization was carried out using 1 mol/l of sodium chloride, 300 ml of a cleaning and disinfecting solution for contact lenses was prepared.

Solubility, appearance, bad smell, pH and viscosity of the cleaning and disinfecting solution for contact lenses were examined in the same manner as in Example 1. The results are shown in Table 1.

Using the cleaning and disinfecting solution for contact lenses instead of the preserving solution for contact lenses in Example 1, the variation coefficient of base curve was calculated in the same manner as in Example 1. The results are shown in Table 1.

COMPARATIVE EXAMPLE 2

In the same manner as in Example 3 except that polyallylamine (1) was not used, 300 ml of a liquid for contact lenses was prepared.

Using the obtained liquid for contact lenses instead of the preserving solution for contact lenses in Example 1, the variation coefficient of base curve was calculated in the same manner as in Example 1. The results are shown in Table 1.

TABLE 1

| | Properties of liquid for contact lenses | | | | | Variation coefficient of base curve of contact lens (%) | |
|---|---|---|---|---|---|---|---|
| | Solubility | Appearance | Bad smell | pH | Viscosity (cP) | After 2 weeks | After 4 weeks |
| Example No. | | | | | | | |
| 1 | A | A | A | 7.2 | 50≧ | 0.1 | 0.2 |
| 2 | A | A | A | 7.2 | 50≧ | 0.1 | 0.2 |
| 3 | A | A | A | 7.2 | 50≧ | 0.1 | 0.2 |
| Comparative Example | | | | | | | |
| 1 | — | — | — | — | — | 0.4 | 0.6 |
| 2 | — | — | — | — | — | 0.4 | 0.8 |

From the results shown in Table 1, it can be understood that all liquids for contact lenses prepared in Examples 1 to 3 have suitable pH and viscosity, show excellent solubility and appearance, and give out no bad smell at all.

It can be understood that when a contact lens is preserved in the liquids for contact lenses prepared in Examples 1 to 3, the variation coefficient of the base curve of the contact lens is remarkably small, of course after preservation for 2 weeks, even after preservation for 4 weeks, compared with preservation in physiological sodium chloride solution in Comparative Example 1 and preservation in the liquid for contact lenses, not containing polyallylamine (1) in Comparative Example 2.

According to United States Pharmacopoeia, the following antiseptic effect test was carried out by the organism challenge test, and the antiseptic and antibacterial properties of the preserving solution for contact lenses prepared in Example 1 was examined.

Into the preserving solution for contact lenses were inoculated $1.0\times10^6$ Gram-positive vegetative bacteria (*Staphylococcus aureus*) and $1.0\times10^6$ Gram-negative vegetative bacteria (*Escherichia coli*). Then, the preserving solution for contact lenses was allowed to stand at 37° C. for 24 hours. After 24 hours, the number of each bacteria in the preserving solution for contact lenses was measured.

As a result, the number of Gram-positive vegetative bacteria and the number of Gram-negative vegetative bacteria were $2.0\times10^3$ and $2.4\times10^3$, respectively, and were remarkably decreased. It can be understood that the preserving solution for contact lenses shows excellent antiseptic effect and excellent antibacterial effect.

In addition to the ingredients used in the Examples, other ingredients can be used in the Examples as set forth in the specification to obtain substantially the same results.

What is claimed is:

1. A liquid for replaceable and removable contact lenses containing from 0.01 to 10 w/v % of a polymer (A) having a recurring unit represented by the formula (I):

(I)

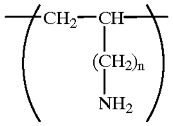

wherein n is 0 or 1, wherein the weight average molecular weight of the polymer (A) is 500 to 200,000, said liquid functioning as a preserving solution, a cleaning solution, a disinfecting solution, or a liquid used for at least two of preservation, cleaning and disinfection.

2. The liquid for contact lenses of claim 1, wherein the polymer (A) is a polyallylamine having a recurring it represented by the formula:

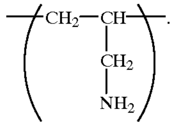

3. The liquid for contact lenses of claim 1, which contains at least one of an antiseptic, a chelating agent, a buffer, an isotonizing agent, a thickener and a surface active agent.

4. In a combination of a removable and replaceable contact lens and a preserving liquid for preserving said contact lens and optionally having a function selected from cleaning, disinfecting and both cleaning and disinfecting said contact lens, wherein said contact lens is submerged in said liquid, the improvement wherein said liquid contains a polymer (A) having a recurring unit represented by the formula (1):

(I)

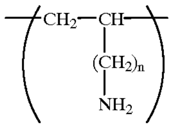

wherein n is 0 or 1, and said polymer has a molecular weight of from 500 to 200,000.

5. The combination of claim 4 wherein said polymer (A) is a polyallylamine having a recurring unit represented by the formula

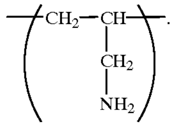

6. The combination of claim 4 wherein the content of the polymer (A) in said liquid is 0.01 to 10 w/v %.

7. The combination of claim 4 wherein said liquid contains at least one of an antiseptic, a chelating agent, a buffer, an isotonizing agent, a thickener and a surface active agent.

8. In a method of at least one of preserving a removable and replaceable contact lens, cleaning said contact lens and disinfecting said contact lens, comprising contacting said contact lens with a liquid for contact lenses to carry out at least one function selected from preserving, cleaning and disinfecting said contact lens, the improvement wherein said liquid for contact lenses contains a polymer (A) having a recurring unit represented by the formula (I):

(I)

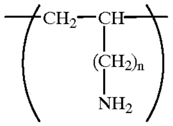

wherein n is 0 or 1, and wherein said polymer has a molecular weight of from 500 to 200,000.

9. The method of claim 8 wherein the polymer (A) is a polyallylamine having a recurring unit represented by the formula (I)

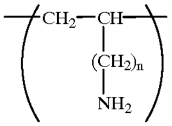

wherein n=1.

10. The method of claim 8 wherein the content of the polymer (A) in said liquid is 0.01 to 10 w/v %.

11. The method of claim 8 wherein said liquid for contact lenses further contains at least one of an antiseptic, a chelating agent, a buffer, an isotonizing agent, a thickener and a surface active agent.

* * * * *